United States Patent [19]
Jakubke et al.

[11] Patent Number: 5,369,018
[45] Date of Patent: Nov. 29, 1994

[54] METHOD OF PRODUCING PEPTIDES

[75] Inventors: Hans-Dieter Jakubke; Dirk Ullmann, both of Leipzig; Karlheinz Drauz, Freigericht; Andreas Bommarius, Frankfurt am Main, all of Germany

[73] Assignee: Degussa Aktiengesellschaft, Germany

[21] Appl. No.: 231,174

[22] Filed: Apr. 22, 1994

[30] Foreign Application Priority Data

Apr. 23, 1993 [DE] Germany .............................. 4313440
Jul. 31, 1993 [DE] Germany .............................. 4325746

[51] Int. Cl.$^5$ ........................ C12P 21/00; C12P 21/02
[52] U.S. Cl. .................................. 435/68.1; 435/212
[58] Field of Search ............................... 435/68.1, 212

[56] References Cited

U.S. PATENT DOCUMENTS 3,972,773  8/1976  Isowa et al. ..................... 435/68.1

FOREIGN PATENT DOCUMENTS

| 1194440 | 1/1985 | Canada ................. 435/68.1 |
| 0272564 | 6/1988 | European Pat. Off. ......... 435/68.1 |
| 0218904 | 2/1985 | Germany ................. 435/68.1 |
| 9119811 | 12/1991 | WIPO ................... 435/68.1 |

OTHER PUBLICATIONS

Biomedica Biochemiga Acta "First International Workshop on Enzymes in Peptide Synthesis" vol. 50 1991 No. 10/11 Bielka et al. Editor pp. 1–265.

Biochemistry Kerr et al. "Catalysis By Serine Proteases and their Zymogens . . . " vol. 14 No. 23 (Nov. 18, 1975) pp. 5088–5094.

*Primary Examiner*—Herbert J. Lilling
*Attorney, Agent, or Firm*—Cushman, Darby & Cushman

[57] ABSTRACT

The biocatalytic production of a peptide is carried out with a zymogen instead of the customarily used protease. Since zymogens are proteolytically inactive precursors of proteases, proteolytic side reactions are largely suppressed. Preferably, amino acid esters or peptide esters and C-terminally derivatized amino acids or peptide fragments are coupled to each other. The reaction can also take place in a frozen, aqueous medium. In particular, chymotrypsinogen, trypsinogen, pepsinogen, prorennin or procarboxypeptidase are suitable as zymogens.

7 Claims, No Drawings

METHOD OF PRODUCING PEPTIDES

The invention relates to a method for the biocatalytic production of peptides and the use of biocatalysts.

BACKGROUND OF THE INVENTION

Various organo-chemical methods can be used to produce peptides (see survey: WUNSCH, E. (1974) Synthesis of Peptides, in HOUBEN-WEYL, vol. 15, ½, Methoden der organischen Chemie, Muller, E. (editor) Georg Thieme Verlag, Stuttgart). Frequently, undesired side reactions are observed in the course of chemical peptide syntheses which reduce the yield and necessitate difficult and prolonged purifying processes. A particularly serious disadvantage of the traditional methods is the unsolved problem of racemization, which occurs especially in segment condensation by means of chemical bonding methods. Since stereoisomers can hardly be completely separated and the optical purity of the synthetics is a necessary prerequisite for their biological activity, the industrial synthesis of peptides by means of organo-chemical methods has considerable disadvantages. Moreover, in all chemical peptide-synthetic operations the tertiary functions of amino-acid structural elements must be masked reversibly because of the risk of side reactions.

The use of biocatalysts for the catalysis of the peptide linking step is available for avoiding the problems described above (see surveys: Jakubke, H. D. (1987) in S. Udenfriend, J. Meienhofer (eds.): The Peptides: Analysis, Synthesis, Biology, vol. 9, Academic New York, pp. 103-165; Kullmann (1987) Enzymatic Peptide Synthesis, CRC, Boca Raton, U.S.A.; Jakubke, H. D., Kuhl, P. and Konnecke, A. (1985) Angew. Chem. 97, 79). Chiral integrity remains preserved because of the stereospecificity of the proteases used as biocatalysts and the high degree of reaction control generally makes it possible to do without the protection of tertiary functions. The kinetically controlled path of the reaction plays a key part within the framework of enzyme-catalyzed peptide synthesis (Schellenberger, V., Jakubke, D. D. (1991) Angew. Chem. 103, 1440). The hydrolysis of the acyl enzyme intermediate, which accompanies formation of the peptide product in this method, and other possible proteolytic splittings, also constitute a problem for many synthetic reactions in that the yield of peptide product remains limited and the separation of by-products renders production more difficult.

SUMMARY OF THE INVENTION

The object of the present invention is to provide a method of biocatalytically producing peptides while minimizing undesired proteolytic side reactions as much as possible.

These and other objects are achieved by a method for the biocatalytic production of a peptide in which a zymogen is used as a biocatalyst.

According to the present invention, the biocatalytic production of a peptide does not take place as is usual with a protease, but rather with a zymogen. Since zymogens are still inactive precursors of proteases and therefore should actually have no catalytic effect, the results of the invention are very surprising. It is advantageous for high yields to use comparably higher concentrations of the selected zymogen. The entire method, that is, selection of the substrates, buffer, medium, temperature, concentrations, reaction time, etc., is relatively non-critical and can be readily determined by an expert in the art for biocatalytic peptide syntheses.

The substrates which are conventional in peptide syntheses with proteases are used for the biocatalytic peptide syntheses of the invention. Optionally N-protected amino-acid esters and/or optionally N-protected peptide esters which are reacted with C-terminally protected amino acids are particularly suitable. The $NH_2$ group of the acyl donor esters is protected, if desired, by amino protective groups which are customarily used in peptide chemistry, such as Boc-, Z-, etc. or by acylation. The following are suitable, for example: maleic acid, acetic acid, benzoic acid, etc. The lower esters in particular are potential candidates for esters; methyl- and ethyl esters as well as methyl cyanide ester, p-nitrobenzyl ester, carboxamidomethyl ester, etc., are especially suitable.

C-terminally derivatized amino acids or peptide fragments, especially amino-acid amides, are advantageously suitable as C-terminal components, and even peptides which are also amides can be used. When using peptides, the C-terminal end can be protected, if desired, e.g. by an $NH_2$ group.

The selection of any derivatizations and initial substrates is basically a function of the desired final product and of the possible requirement of preventing side reactions. This selection is therefore within the skill of persons experienced in the art.

The method of the invention provides, as compared with the previous use of proteases, the particular advantage of suppressing undesired proteolytic splitting reactions. This is successful, according to the invention, because the zymogen exhibits a new specificity in relation to the corresponding protease. This makes it possible to select, for a desired peptide structure, a zymogen which, on the one hand, is suitable for building up the peptide from the substrates in an acceptable time and yield and which, on the other hand, corresponds with such an enzyme for which the peptide obtained is preferably not a substrate. That is, the rate of peptide formation produced by the zymogen should be at least one order of magnitude more rapid than the peptide degradation induced by the enzyme corresponding to the zymogen. In other words, the zymogen is preferably selected in such a manner that the linking rate of the substrates selected is preferably ten times greater that the rate of the peptide degradation by the enzyme corresponding to the zymogen. It is thus possible, for example, to convert "chymotrypsin-specific" substrates with trypsinogen or "trypsin-specific" substrates with chymotrypsinogen. This prevents the corresponding enzyme accompanying the zymogen to a slight degree, or even enzyme produced during the synthesis by limited proteolysis from the zymogen, from causing a reverse reaction. This type of secondary hydrolysis can be largely or totally stopped by this method.

Chymotrypsinogen, trypsinogen, pepsinogen, prorennin or pro-carboxypeptidase is preferably used as zymogen.

According to the invention, peptides are preferably produced from a free or α-amino-group-protected amino acid, or from a free or α-amino-group-protected peptide, whose carboxyl group entering into reaction is present as ester, and from an amino acid, an amino-acid derivative or a peptide in which the amino acid entering in reaction is not blocked at the $NH_2$ end in the presence of the zymogen, e.g. of the zymogen of a serine protease in solution or suspension at room temperature which contains, if necessary, components of organic solvents and/or buffer substances or also at lower temperatures.

The reaction is preferably carried out in an aqueous medium which can optionally contain components of organic solvents; low temperatures are potentially advantageous, at which the aqueous medium can also be frozen to ice, since, in addition, the secondary hydrolysis can be suppressed when the method of the invention is carried out at low temperatures.

The peptides formed can be separated in a preparative manner with suitable chromatographic or extractive techniques. After termination of the workup, any protective groups still present can be removed using known methods.

Those can also be used as buffer which inhibit proteolytic reactions. This can also reduce undesired secondary hydrolyses.

In contrast to known methods for the synthesis of peptides using proteases, the danger of undesired splittings is significantly reduced by the use, in accordance with the invention, of proteolytically inactive proenzymes. For the first time for the class of peptide substances, their biocatalytic synthesis with zymogens is performed. The effect of the invention is surprising, since the formation of a peptide bond could not have been expected with proteolytically inactive proenzymes. In the presence of small amounts of active protease species in the zymogens used, a possible proteolytic side reaction is substantially excluded by lowering the temperature or freezing of the reaction in a known manner: That is, in particular, the zymogens which are commercially available and usually contain low percentages by weight of the corresponding enzyme can be used with the method variants just described.

The present invention provides novel possibilities of use for zymogens; the invention therefore also includes the use of a zymogen for peptide synthesis as well as including the use of a zymogen as such as biocatalyst. The term "zymogen as such" denotes that the zymogen itself, optionally supported by other components, acts as biocatalyst and that the reaction does not proceed by producing the corresponding protease at first from the zymogen by limited proteolysis which then biocatalyzes the reaction without the cooperation of the zymogen.

The peptides or peptide derivatives which can be produced with the present invention are suitable, optionally after splitting of protective groups, e.g. as active substances or intermediate products of active substances.

DETAILED DESCRIPTION OF PREFERRED EMBODIMENTS

The present invention is explained in detail in the following examples.

The amino acids are abbreviated in the examples in accordance with internationally accepted rules. The following abbreviations are also used:

| | |
|---|---|
| Ac | acetyl |
| Bz | benzoyl |
| Boc | tert.-butyloxycarbonyl |
| Mal | maleyl |
| OCam | carboxamidomethyl ester |
| OEt | ethyl ester |
| OMe | methyl ester |
| NH$_2$ | amide |

Unless otherwise noted, amino acids or amino-acid groups with chiral center exhibit an L-configuration.

EXAMPLE 1

Synthesis of Mal-Phe-Leu-NH$_2$ a) with trypsinogen 2 ml 0.05M borate buffer, pH 9, containing 0.2M NaCl, 2 mM Mal-Phe-OMe, 50 mM H-Leu-NH$_2$ and 4 μM trypsinogen are agitated at 25° C. under pH control. After 24 hours, the reaction solution is brought to pH 2 with 0.5% trifluoroacetic acid in methanol/water (1:1; v/v). The yield is analytically determined with HPLC to be 73.5% of theory.

If the synthesis is not carried out at room temperature, but rather at −15° C. in a frozen aqueous system, the yield, after 24 hours at a C/N ratio of 1:10, is then 87% of theory or at a C/N ratio of 1:5, it is 77% of theory.

b) with chymotrypsinogen

The procedure of Example 1a is repeated, but with 4 μM chymotrypsinogen as biocatalyst. Yield after 24 hours: 82% of theory. A reference batch resulted, after 48 hours, in a yield of 80.3% of theory.

If the synthesis is carried out under pH star conditions (KOH; pH 8.5) in the absence of borate buffer and NaCl, the yield after 2 hours is then 83% of theory. A reference batch resulted, after 72 hours, in an unchanged yield.

EXAMPLE 2

Synthesis of Mal-Phe-Leu-Leu-NH$_2$ 2 ml 0.05 borate buffer, pH 9, containing 0.2M NaCl, 2 mMMal-Phe-OMe, 50 mM H-Leu-Leu-NH$_2$ and 12 μM trypsinogen are agitated at 25° C. under pH control. The reaction is stopped as described in Example 1a. After 24 hours, the yield, analytically determined with HPLC, is 61% of theory. A parallel batch resulted, after 48 hours, in a yield of 60.3% of theory.

EXAMPLE 3

Synthesis of Mal-Phe-Phe-Leu-NH$_2$ 1 ml 0.1M veronal-Na/HCl buffer, pH 8.3/56% (v/v) DMSO, containing 40 mMMal-Phe-Phe-OCam, 120 mM H-Leu-NH$_2$ and 40 μM trypsinogen is agitated at room temperature under pH control. After 85 minutes, the reaction solution is stopped with 2% acetic acid. The yield is determined analytically with HPLC and is 72% of theory.

EXAMPLE 4

Synthesis of Boc-Phe-Leu-NH$_2$ 1 ml 0.1M veronal-Na/HCl buffer, pH 8.3/50% (v/v) DMSO, containing 100 mM Boc-Phe-OCam, 300 mM H-Leu-NH$_2$ and 100 μM trypsinogen is agitated at room temperature under pH control. After 3 hours, the reaction is stopped as described in Example 3. The yield is analytically determined with HPLC to be 93% of theory.

EXAMPLE 5

Synthesis of Ac-Tyr-Leu-NH$_2$ a) with chymotrypsinogen 0.5 ml 0.05M borate buffer, containing 0.2M NaCl, 2 mM Ac-Tyr-OEt 50 mM H-Leu-NH$_2$ and 4 μM chymotrypsinogen are agitated at 25° C. under pH control. The reaction is stopped as described in Example 1a.

After 30 minutes, the yield, determined analytically with HPLC, is 83.5%. A parallel batch resulted, after 1 hour, in the same yield whereas it was only 59% of theory after 68-hours reaction time.

If, on the other hand, the synthesis is carried out under the same conditions, but at −15° C. in a frozen state, the yield is then 93% of theory after 24 hours.

b) with trypsinogen

The procedure of Example 5a is used, but with 12 μM trypsinogen as biocatalyst. Yield after 10 minutes: 76% of theory. Whereas parallel batches resulted in the same yields after 30 minutes and 60 minutes, after 68 hours only 66% of theory was obtained.

If, on the other hand, the synthesis is carried out at −15° C. in a frozen state, after 1 hour, 45% and after 24 hours even 93% of theory are obtained.

EXAMPLE 6

Synthesis of Bz-Arg-Leu-NH$_2$ a) with trypsinogen 2 ml 0.05M borate buffer, pH 9, containing 0.2M NaCl, 2 mM Bz-Arg-OEt, 50 mM H-Leu-NH$_2$ and 4 μM trypsinogen are agitated at 25° C. under pH control. The reaction is stopped as described. After 5 minutes, the yield, determined analytically with HPLC, is 72% of theory. Parallel batches resulted, after 1 hour and after 24 hours, in 62% and 0% yield.

If the synthesis is not carried out at 25° C. but rather at −15° C., in a frozen state, the yield is then 93% of theory after 1 hour. A parallel batch also resulted after 24 hours, under the same conditions, in 93% yield.

b) with chymotrypsinogen

The procedure of Example 6a is used, but with 25 μM chymotrypsinogen as biocatalyst. The yield, determined analytically with HPLC, is 50% of theory after 24 hours at room temperature, and 66% of theory after 72 hours.

EXAMPLE 7

Synthesis of Bz-Arg-Ala-Ile-OH a) with trypsinogen 2 ml 0.05M borate buffer, pH 9, containing 0.2M NaCl, 2 mMMal-Phe-OMe, 50 mM H-Ala-Ile-OH and 4 μM trypsinogen are agitated at 25° C. under pH control. The reaction is stopped as described. After 10 minutes, the yield is 68% of theory. Parallel batches resulted, after 1 hour and after 24 hours, in 58% and 0% yield.

If the synthesis is not carried out at 25° C., but rather at −15° C. in a frozen state, the yield is then 76% of theory after 1 hour. A parallel batch resulted, after 24 hours, in an similar yield.

b) with chymotrypsinogen

The procedure of Example 7a is repeated, but with 4 μM chymotrypsinogen as biocatalyst. The yield is 65% after 24 hours and 68% of theory after 72 hours.

EXAMPLE 8

Synthesis of H-Phe-Arg-NH$_2$ a) with chymotrypsinogen 1 ml 0.05 m veronal sodium carbonate buffer, pH 9, containing 0.2M NaCl, 2 mM Phe-OMe, 50 mM Arg-NH$_2$ and 10 μM chymotrypsinogen are agitated at room temperature. After 4 hours, the reaction is stopped with 2.5% trifluoroacetic acid. The yield is determined analytically with HPLC and is 77% of theory. A parallel batch resulted, after 24 hours, in an unchanged yield.

b) with trypsinogen

The procedure of Example 8a is repeated, but with 10 μM trypsinogen. The yield is 61% of theory after 4 hours.

What is claimed is:

1. In a method for the biocatalytic production of a peptide in the presence of a biocatalyst; the improvement in which the biocatalyst is a zymogen.

2. A method according to claim 1 in which the peptide is built up from an amino acid ester or from a peptide ester and a C-terminally derivatized amino acid or from a peptide fragment.

3. A method according to claim 1 or 2 in which the rate of the peptide degradation by the enzyme corresponding to the zymogen is at least one order of magnitude slower than the linking rate of the substrates in the presence of the zymogen.

4. A method according to claim 1 or claim 2 in which the reaction is carried out in an aqueous medium.

5. A method as set forth in claim 4 in which the aqueous medium contains a portion of an organic solvent.

6. A method according to claim 4 in which the reaction is carried out in a frozen aqueous medium.

7. A method according to claim 1 or claim 2 in which the zymogen is selected from the group consisting of chymotrypsinogen, trypsinogen, pepsinogen, prorennin and pro-carboxypeptidase.

* * * * *